(12) United States Patent
Graham

(10) Patent No.: US 6,534,769 B1
(45) Date of Patent: Mar. 18, 2003

(54) LOW COST MAIN STREAM GAS ANALYZER SYSTEM

(75) Inventor: James E. Graham, Brookfield, WI (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 0 days.

(21) Appl. No.: 09/477,914

(22) Filed: Dec. 31, 1999

(51) Int. Cl.[7] .............................................. G01N 21/01
(52) U.S. Cl. ..................................................... 250/343
(58) Field of Search ............................. 250/343, 353; 600/532; 128/204.4

(56) References Cited

U.S. PATENT DOCUMENTS

| | | | |
|---|---|---|---|
| 5,042,522 A | 8/1991 | Corenman et al. | 137/239 |
| 5,063,275 A | 11/1991 | Rosenfeld et al. | 250/343 |
| 5,092,342 A | 3/1992 | Hattendorff et al. | 600/532 |
| 5,159,199 A * | 10/1992 | LaBaw | 250/339.02 |
| 5,159,934 A | 11/1992 | Hoberman | 600/532 |
| 5,282,473 A | 2/1994 | Braig et al. | 600/532 |
| 5,296,706 A | 3/1994 | Braig et al. | 250/339.13 |
| 5,309,921 A * | 5/1994 | Kisner et al. | 128/925 |
| 5,355,893 A | 10/1994 | Mick et al. | 600/532 |
| 5,401,966 A * | 3/1995 | Gray et al. | 250/343 |
| 5,931,161 A | 8/1999 | Keilbach et al. | 128/204.22 |
| 5,932,877 A | 8/1999 | Braig et al. | 250/343 |
| 6,044,843 A | 4/2000 | O'Neil et al. | 128/204.23 |
| 6,138,674 A * | 10/2000 | Gull et al. | 128/204.21 |
| 6,190,327 B1 * | 2/2001 | Isaacson et al. | 600/529 |

FOREIGN PATENT DOCUMENTS

EP   0 825 430 A2   2/1998

* cited by examiner

Primary Examiner—Constantine Hannaher
Assistant Examiner—Shun Lee
(74) Attorney, Agent, or Firm—Foley & Lardner; Carl B. Horton (57) ABSTRACT

A gas stream monitoring system including a low cost main stream gas analyzer system is disclosed herein. The low cost main stream gas analyzer system is calibrated by a side stream gas analyzer system included in the gas stream monitoring system. Once calibrated, the side stream system is placed into standby mode such that diversions of portions of the gas stream can be minimized. The calibrated output signals from the low cost main stream system contain corrections for gas interference, pressure change, temperature change, manufacturing tolerance, component flaws, and any other sources of error.

19 Claims, 5 Drawing Sheets

LOW COST MAIN STREAM GAS ANALYZER SYSTEM

BACKGROUND OF THE INVENTION

The present invention relates generally to gas analyzer systems and methods of manufacturing same. More particularly, the present invention relates to a main stream gas analyzer system capable of determining carbon dioxide concentrations using low cost components.

In many applications, it is desirable to identify and monitor the concentrations of components in gas streams. For example, in the field of anesthesiology, it is often desirable to monitor the concentrations of various gaseous anesthetic or therapeutic agents, such as nitrous oxide, halothane, enflurane, desflurane, sevoflurane, and isoflurane, being dispensed to be inhaled by a patient and/or being exhaled by the patient. Moreover, it is common to continuously monitor and display the carbon dioxide ($CO_2$) concentration relating to a patient because $CO_2$ concentration is a good indicator of the patient's ventilation. $CO_2$ in the bloodstream equilibrates rapidly with $CO_2$ in the lungs, and hence, partial pressure of $CO_2$ in the lungs is a fair approximation of $CO_2$ level in the blood, especially the $CO_2$ content at the end of each breath, i.e., the end-tidal $CO_2$. Accordingly, abnormally end-tidal $CO_2$ level indicates poor blood flow to the tissues, inadequate $CO_2$ transport through the lungs, or excessive ventilation. Conversely, abnormally high end-tidal $CO_2$ level indicates that an insufficient amount of $CO_2$ is being transported away from the bloodstream through the lungs, i.e., inadequate ventilation.

Presently, there are two types of non-dispersive infrared (IR) gas analyzers for determining gas concentrations: (1) side stream gas analyzers and (2) main stream gas analyzers. Side stream gas analyzer systems divert or draw off a portion of the patient's inspired and expired respiratory gases from a patient's airway of a patient circuit. This portion, or gas sample, is then transported to a distal site for analysis by a side stream gas analyzer. The analyzed gas sample is either returned to the patient.circuit or disposed of altogether.

In contrast, main stream gas analyzer systems are configured to use a portion of the patient's airway as the sampling cell. Hence, there is no diversion of any of the gases going to or coming from the patient. A main stream gas analyzer system includes a short length of specially configured tube, i.e., an airway adapter, at the patient's airway to act as the sampling cell. The main stream gas analyzer couples to this airway adapter such that optical and electronic components comprising the analyzer can monitor the patient's airway. As the patient's respiratory gases travel through the airway adapter, the desired gas, such as $CO_2$, is monitored.

Side stream devices have a number of attractive features such as the ability to simultaneously analyze a plurality of gases comprising the gas sample; lack of device weight and size constraints; the ability to correct for gas pressure changes and the presence of interfering gases; and the ability to self-calibrate. On the other hand, having to divert a portion of the patient's respiratory gases to use as the gas sample and also having to transport the gas sample to a distal site for the actual analysis (typically ten or more feet via a transport tube) causes distortion in the gas sample and within the patient circuit.

For example, water vapor in the gas sample will condense in the transport tube because of the change in surrounding temperature from body temperature (approximately 37° C.) to room temperature (approximately 23° C.). This necessitates extensive water handling systems and causes further distortion of the gas sample. Another problem is the mixing of successive gas samples as they travel toward the side stream analyzer. When an inspired gas sample mixes with an expired gas sample, information relating to actual conditions in the patient's airway such as the inspiration-expiration transition may be lost or distorted. Still another problem is the handling of gas samples after they have been analyzed. If "spent" gas samples are returned to the patient circuit, they will pass through a common device, which may be contaminated by a previous patient. Thus, care must be taken to insure that returning gas samples are filtered to remove any such contaminates. Alternatively, if "spent" gas samples are disposed of altogether, some of the gases, such as anesthetic agents, that are intentionally dispensed to the patient will be lost. Not only are some of these gases quite expensive, but the removed gases must be monitored and be compensated for within the patient circuit so that the patient would actually be receiving the-proper amount of anesthetic agents.

Main stream devices similarly have its own advantages and disadvantages. Advantages include: (1) no distortion of gas samples because there is no diversion from nor interference with the patient circuit; (2) continuous monitoring; (3) fast response; and (4) negligible time delay from sampling to measurement display. On the other hand, because no isolated amount of gas is ever used for analysis, it is difficult to provide accurate absolute measurements. Typically, only one gas can be monitored by each main stream device. Thus, unlike side stream devices, concentrations of other gases and interference from these gases, if any, cannot be corrected. Another shortcoming is the inability to correct for pressure change. Total pressure in the patient's airway cannot be measured and thus, pressure changes caused by compressor cycles cannot be taken into account. Still another shortcoming is that main stream devices must be small and lightweight such that it can attach onto the airway adapter without causing discomfort to or traction on the patient's airway. It becomes very complicated and expensive to maintain the necessary dimension constraints when compensation and calibration components must also be included in order to provide a self-sustaining main stream device.

Using both types of gas analyzers would be preferable, but it is rarely done due to the prohibitive cost of each type of gas analyzer. Instead, practitioners or operators will purchase one or the other depending on the feature that is most desirable. Thus, there is a need for a main stream gas analyzer system that is small, lightweight, and inexpensive. There is a further need for a main stream gas analyzer system that is inexpensive enough to be readily used in conjunction with a side stream device. Even still further, there is a need for a main stream gas analyzer system that reduces the need to continually draw off gas samples from the patient circuit for calibration purposes, as is commonly done when the side stream device is used alone.

BRIEF SUMMARY OF THE INVENTION

One embodiment of the invention relates to a low cost main stream gas analyzer system. The system includes an airway adapter including an entering plastic window and an exiting plastic window to permit non-invasive monitoring of a gas stream. The system further includes a gas analyzer coupled to the airway adapter and including a reflector. The reflector comprises a plastic component with a reflective coating.

Another embodiment of the invention relates to a low cost main stream gas analyzer system. The system includes means for interfacing with a gas stream. The means for interfacing includes an entering plastic window and an exiting plastic window to permit non-invasive monitoring of the gas stream. The means for analyzing is coupled, to the means for interfering. The means for analyzing includes a means for reflecting. The means for reflecting comprises a plastic component with a reflective coating.

Another embodiment of the invention relates to a gas analyzing system. The system includes a gas stream of interest, and a side stream system coupled to the gas stream of interest. The system further includes a main stream system coupled to the gas stream of interest. The main stream system is configured to be an inexpensive analyzer capable of placing the side stream system on standby mode. The side stream system is configured to go into active mode as needed to divert a portion of the gas stream of interest to perform calibration of a sensed signal outputted from the main stream system.

BRIEF DESCRIPTION OF THE DRAWINGS

The preferred embodiment will become more fully understood from the following detailed description, taken in conjunction with the accompanying drawings, wherein like reference numerals denote like elements, in which.

DETAILED DESCRIPTION OF THE INVENTION

Figure 1:
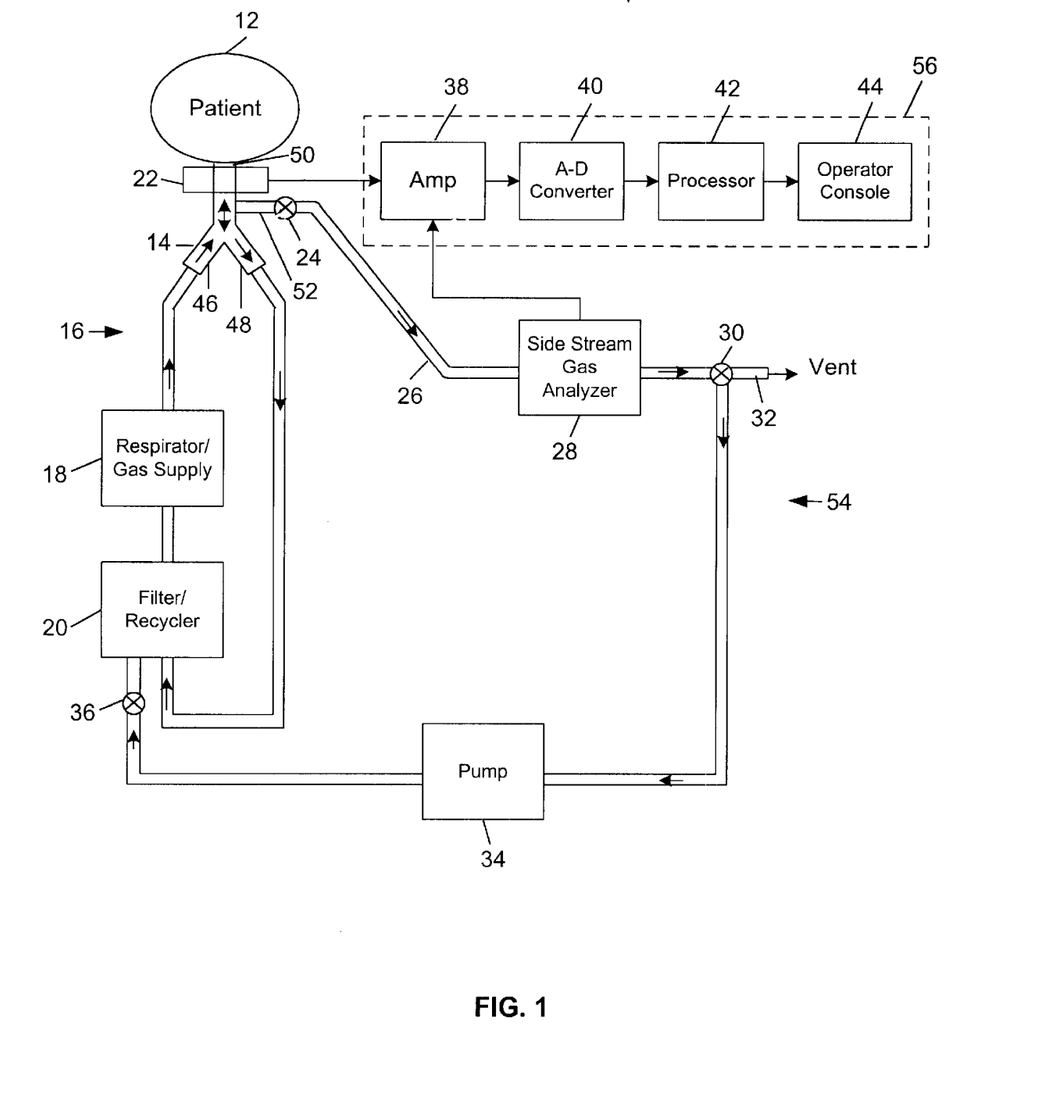
FIG. 1 is a block diagram of a patient respiratory monitoring system.
Figure 2:
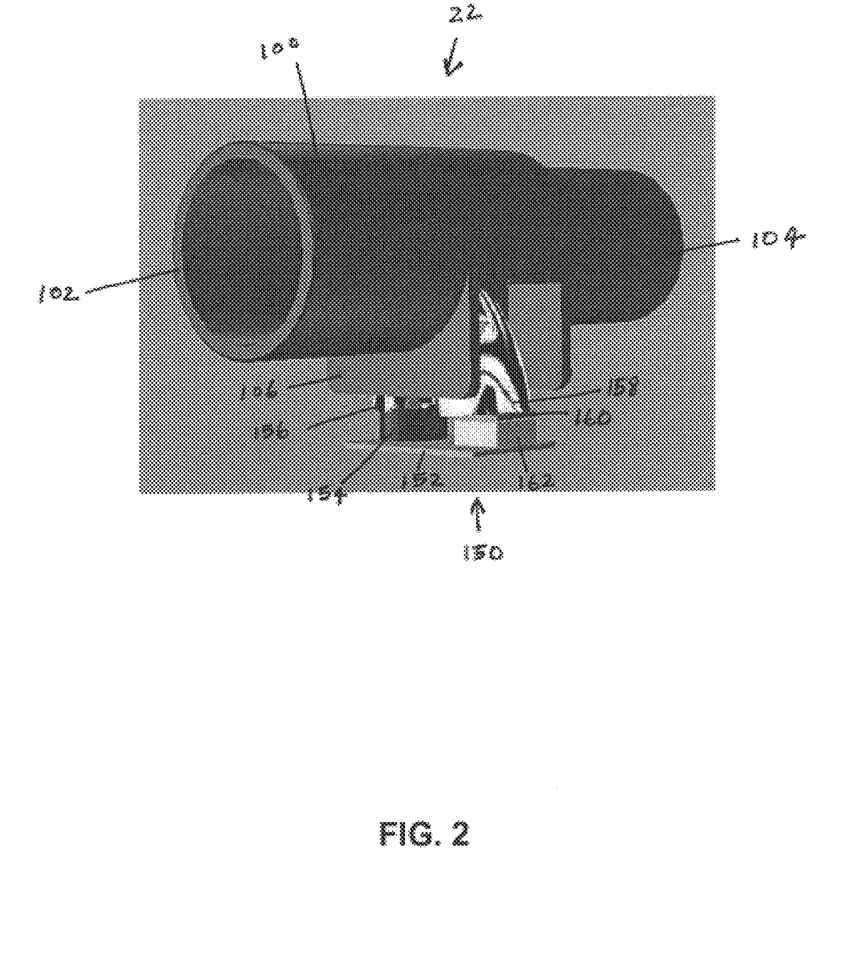
FIG. 2 is a perspective view of a main stream gas analyzer system which forms part of the patient respiratory monitoring system of FIG. 1.

Referring to FIG. 1, there is shown the major components of a patient respiratory monitoring system 10. Patient respiratory monitoring system 10 is configured to provide and monitor inspiratory gases to a patient 12 and to monitor gas concentrations of respiratory gases, thereby providing information regarding the patient's 12 condition. System 10 includes a patient respiratory circuit 16, a side stream circuit 54, a gas concentration generation unit 56, and a main stream gas analyzer system 22.

Patient respiratory circuit 16, which provides a desired mixture of inspiratory gases to patient 12, includes the patient 12, an airway tube 14, a respirator/gas supply 18, and a filter/recycler 20. Patient 12 interfaces with airway tube 14, and the airway tube 14 is coupled to filter/recycler 20. Filter/recycler 20 is coupled to respirator/gas supply 18, and respirator/gas supply 18 is coupled to airway tube 14, thereby completing the loop.

Patient 12 interfaces with airway tube 14 via a mouthpiece, intratracheal tube, or anesthesia mask (not shown). Airway tube 14 includes an inlet 46, an outlet 48, and a port 50. Airway tube 14 includes appropriate one-way valves, such as check valves, to permit one-way flow of inspiratory gases from respirator/gas supplier 18 to patient 12, via inlet 46 and port 50; and one-way flow of expiratory gases from patient 12 to filter/recycler 20, via port 50 and outlet 48. Airway tube 14 is shown as an Y-shaped tube. Alternatively, air way tube 14 can be of other shapes and configurations, such as a T-shape, as long as it can perform the functions described herein.

Respirator/gas supply 18 provides inspiratory gases to patient 12 via inlet 46 of airway tube 14. Inspiratory gases may include therapeutic agents, anesthetic agents, nitric oxide, oxygen, carbon dioxide ($CO_2$), radioactively tagged particle, and/or various other gaseous agents. Respirator/gas supply 18 includes gas canisters, gauges, valves, controllers, and other components to provide the desired gas mixture to patient 12.

Filter/cycle 20 receives expiratory gases from patient 12 via outlet 48 of airway tube 14. Expiratory gases can be a mixture of patient's 12 expired gases (such as $CO_2$), recovered inspiratory gases, and harmful materials (such as microprobes and other contaminants). Filter/recycle 20 removes undesirable components, such as harmful materials, from the expiratory gases, to respirator/gas supply 18 for reuse. It is contemplated that patient respiratory circuit 16 may further include additional components such as a compressor to regulate the pressure and flow rate of gas streams within the patient respiratory circuit 16.

Side stream circuit 54 includes a side stream diverter tube 52, a first valve 24, a side stream transport tube 26, a side stream gas analyzer 28, a second valve 30, a vent 32, a pump 34, and a return tube 30. An airway adapter 100, coupled to airway tube 14, includes an aperture at port 50 to receive the side stream diverter tube 52. Alternatively, side stream diverter tube 52 may comprise an integral part of airway tube 14. Side stream diverter tube 52 is coupled to first valve 24, and first valve 24 is coupled to side stream transport tube 26. Side stream transport tube 26 is coupled to side stream gas analyzer 28, and side stream gas analyzer 28 is coupled to pump 34. Pump 34 is coupled to vent 32 or, alternatively, to return tube 30.

Side stream diverter tube 52 can be a tube of ten feet or more in length and as such, water vapor in the diverted gas sample can condense inside tube 52. Although not shown, side stream circuit 54 may include a water handling system. First valve 24 is an one-way valve configured to permit a portion of respiratory gases in port 50 to be diverted or drawn off from patient respiratory circuit (via side stream diverter tube 52) or to take in room air. Air First valve 24 may be a computer controlled solenoid-operated globe or gate valve such that portions of respiratory gases need to be diverted from patient respiratory circuit 16 only when gas samples are required for analysis by side stream gas analyzer 28. Each diverted gas sample can include inspiratory and/or expiratory gases. At all other times, air is sampled for auto-zeroing functions.

The diverted gas sample travels from first valve 24 to side stream gas analyzer 28, via side stream transport tube 26. Side stream transport tube 26 may be ten feet or longer and as such, water vapor in the diverted gas sample can condense inside side stream transport tube 26. Although not shown, side stream circuit 54 can include a water handling system.

The diverted gas sample then travels from air valve 24 to side stream gas analyzer 28 for analysis, via side stream transport tube 26. After the diverted gas sample has been analyzed by side stream gas analyzer 28, it can either be disposed of via vent 32 or returned to patient respiratory circuit 16 via third valve 36. Second valve 30 is configured to direct the diverted gas sample to vent 32 or third valve 36. Second valve 30 may be a three-port, two-way valve as is well-known in the art.

Pump 34 is configured to cause the diverted gas sample to travel through side stream circuit 54. Actuation and/or positions of second valve 30 and pump 34 may be coordinated with each other such that undesirable gas flow and pressure problems do not occur in side stream circuit 54. For example, when second valve 30 is positioned to dispose of the diverted gas sample, pump 34 may need to be cycled off. Furthermore, pump 34 may be positioned at different points within side stream circuit 54 then as shown in FIG. 1.

Side stream gas analyzer 28 is coupled to the gas concentration generation circuit 56, to be described in greater detail hereinafter, and is configured, among others, to measure the gas.concentrations of one or more component gases comprising each diverted gas sample; correct measured gas concentrations for pressure changes; correct measured gas concentrations for the effect of interfering gases; and self-calibrate, as needed, to compensate for changing conditions such as changing room temperature.

Gas concentration generation unit 56 includes a signal amplifier 38, an analog-to-digital (A-D) converter 40, a processor 42, and an operator console 44. Signal amplifier 38 is coupled to the A-D converter 40, A-D converter 40 is coupled to processor 42, and processor 42 is coupled to the operator console 44. The output of the main stream gas analyzer system 22 or the side stream gas analyzer 28 is the input to signal amplifier 38.

Signal amplifier 38, also referred to as a signal buffer, amplifies the analog signals from either of systems 22, 54 such that it can be converted into a digital signal by A-D converter 40. The digital signal outputted by A-D converter 40 is the input to processor 42.

Processor 42 uses the digital signals to output a correlated gas concentration signal. The calculation of gas concentration signal also takes into account calibration adjustments and other necessary adjustments to generate an accurate gas concentration signal. The gas concentration signal is lastly outputted to operator console 44 for real-time or quasi-real-time viewing by a user. Operator console 44 may also include a storage unit to record gas concentration signals over a period of time, and manipulation tools to manipulate the displayed information and/or to effect the functions of main stream gas analyzer system 22 or side stream circuit 54.

Referring to FIGS. 2–5, there is shown main stream gas analyzer system 22 including an airway adapter 100 and a main stream device 150. Main stream device 150 couples to airway adapter 100, to be described in greater detail hereinafter, and main stream device 150 is preferably enclosed by a protective housing (not shown).

Figure 3:
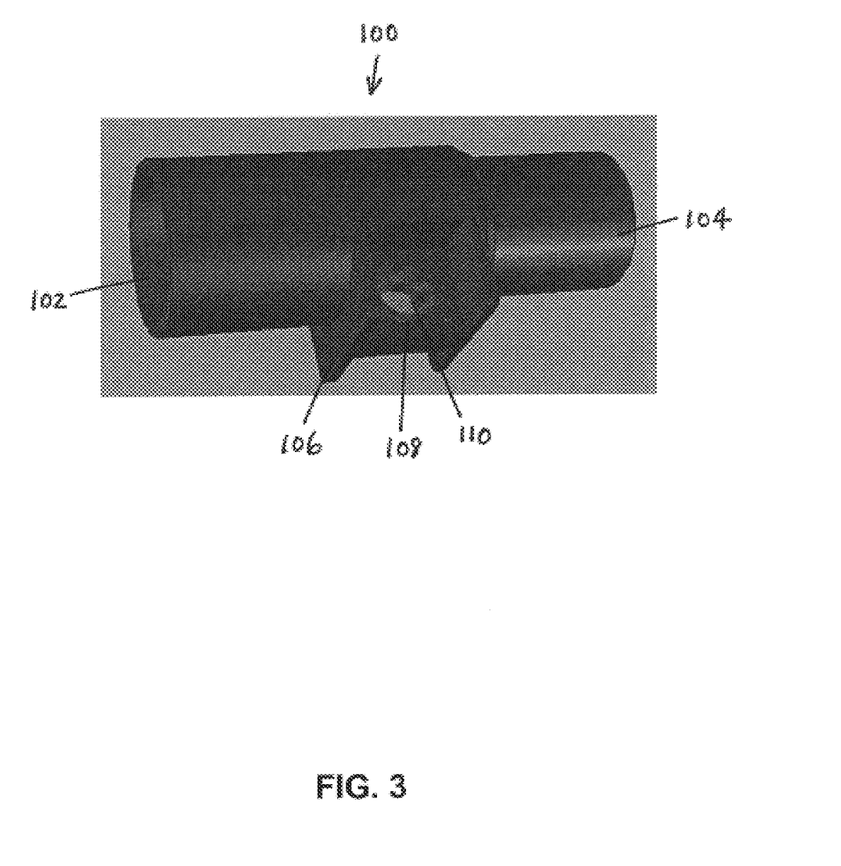
FIG. 3 is a perspective view of an airway adapter which forms part of the main stream gas analyzer'system of FIG. 2.

Airway adapter 100 comprises a short length of a specially shaped tube including a first end 102, a second end 104, a connection section 106, and a pair of apertures 108. First and second ends 102, 104 comprise the two opposite ends of airway adapter 100, both lying along a central axis running through airway adapter 100. First and second ends 102, 104 are the connection points i.e., standarized connection points as is well-known in the art, to the patient's airway. Preferably, airway adapter 100 is coupled between patient 12 and airway tube 14, and more preferably between a mouthpiece, intubation tube, or mask and airway tube 14.

Connection section 106, located between first and second ends 102, 104, includes a cutout-like section including apertures 108 to permit undisturbed sampling of the patient's respiration by main stream device 150. Apertures 108 are symmetrical with respect to the central axis running through airway adapter 100 and lies along a plane oriented perpendicular to this central axis.

The overall dimensions (e.g., diameters of first and second ends 102, 104), the fabrication technique (e.g., molded one-piece construction), and the materials (e.g., plastic) comprising-airway adapter 100 are well-known in the art. However, in one embodiment, apertures 108 are covered by windows 110. Each window 110 seals aperture 108 such that gases do not leak out of airway adapter 100. Window 110 is an optically transparent material capable of permitting transmittance of photonic energy at a certain wavelengths. The material comprising window 110 need not provide 100% transmittance at these wavelengths nor does it need to only transmit photonic energy at these wavelengths. Any of a variety of materials, especially low cost materials satisfying the above conditions, are suitable for window 110.

For example, to monitor carbon dioxide ($CO_2$) concentration using system 22, window 110 should provide transmittance at 4.26 micrometer, a $CO_2$ absorption wavelength point. Window 110 can be a plastic film such as polycarbonate. Polycarbonate is a very inexpensive and readily accessible material; moreover, polycarbonate providers appreciable transmittance at and around the 4.26 micrometer $CO_2$ absorption point. (The transmittance properties at other wavelengths are of little importance.) In fact, window 110 could even be a plastic-type sticker. Alternatively, when other gases are being monitored using system 22, window 110 should be chosen a accordingly to have desirable transmittance properties at the absorption wavelengths of these other gases.

Apertures 108 and windows 110 can be of any shape, such as circular, rectangular, etc., and preferably have a diameter approaching approximately 0.5 inch. Having a relatively large window decreases focusing requirements of main stream device 150. The thickness of window 110 depends partly on the diameter of each of apertures 108. The pressure inside airway adapter 100 is approximately 100 centimeters of water pressure per square inch higher than atmospheric pressure. So the larger the diameter of each of apertures 108, the greater the total pressure against windows 110. If either of windows 110 is too thin, too much pressure could cause it to bulge like a balloon (i.e., deform) or even rupture. However, for windows 110, the thicker the material, the greater the amount of attenuation of the transmitted photonic energy. Thus, thickness of windows 110 can vary depending on the type of material, the diameter of apertures 108, and transmittance requirements.

Figure 4:
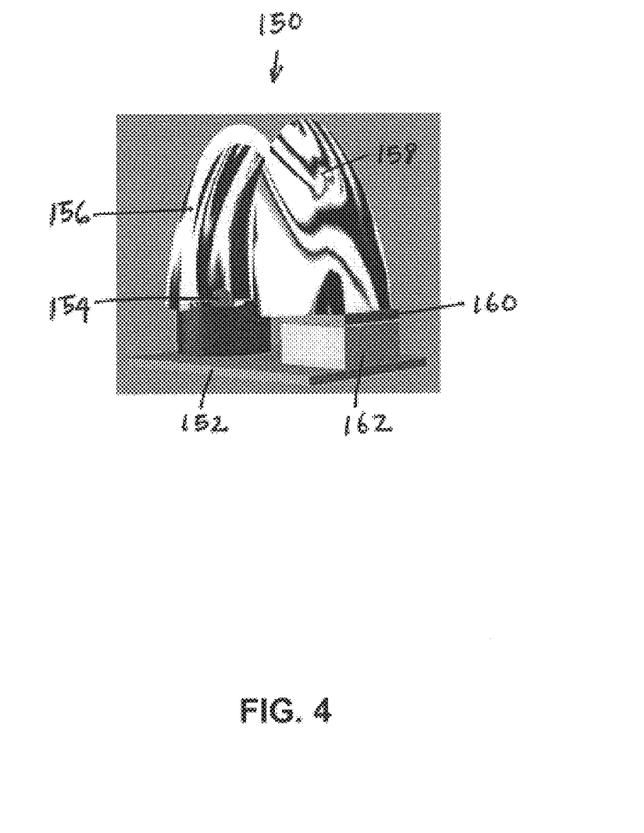
FIG. 4 is a perspective view of a main stream device which forms part of the main stream gas analyzer system of FIG. 2.

Main stream device 150 includes a base 152, an infrared (IR) source 154, a first reflector 156, a second reflector 158, an interference filter 160, and a detector 162. IR source 154 and detector 162 are mounted to the top of base 152. First reflector 156 is coupled above IR source 154 and second reflector 158 is similarly coupled above detector 162, with interference filter 160 sandwiched between second reflector 158 and detector 162. Thus, an optical pathway can be subscribed from IR source 154, first reflector 156, second reflector 158, interference filter 160, and lastly to detector 162.

Base 152 is preferably a printed circuit board configured to provide power to mainstream device 150. Base 152 may include signal processing circuitry and other types of circuitry. IR source 154 is configured to provide an IR energy beam 200 (see FIG. 5) of approximately 0.6 Watts to initiate analysis of the patient's respiratory gases. IR source 154 is preferably an IR source sub-miniature lamp; alternatively, IR source 154 may be other IR sources such as a light bulb or diode capable of IR light output.

Figure 5:
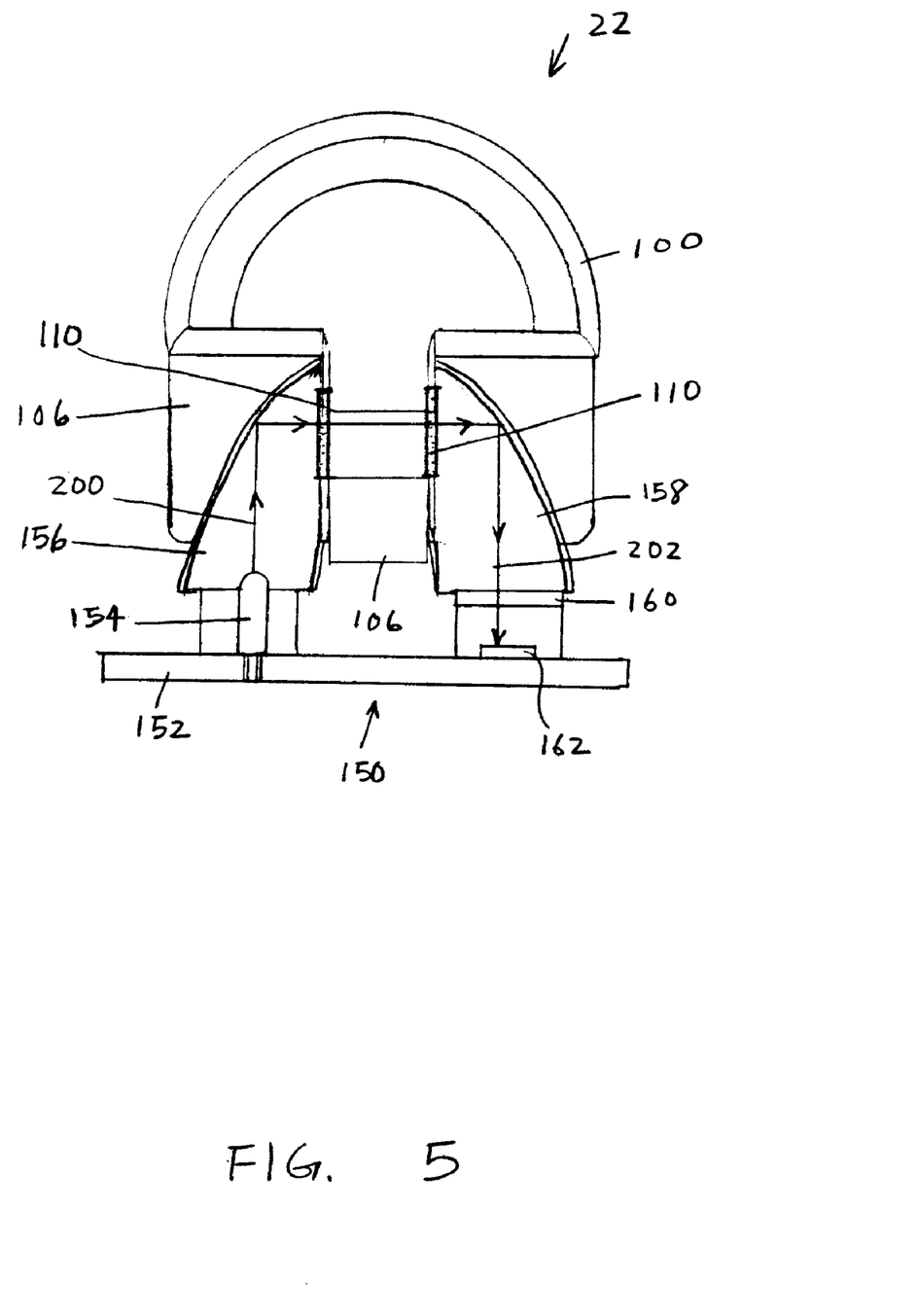
FIG. 5 is a cross-sectional view of the main stream gas analyzer system of FIG. 2.

First and second reflectors 156, 158 are configured to focus and reflect IR energy beam 200 from IR source 154 through window 110, and then reflect an altered IR energy beam 202 exiting window 110 to detector 162, respectively (see FIG. 5). Accordingly, first and second reflectors 156, 158 can be of any shape as long as they are capable of performing the focusing and reflecting functions with respect to beams 200, 202. For example, first and second reflectors 156, 158 can have a parabolic-like shape (or a portion of a parabola) and face each other as shown in FIGS. 3–4. Moreover, reflectors 156, 158 can be made of molded plastic with a reflective coating added to at least the inwardly facing curved sides. The reflective coating maybe an aluminum coating deposited using vapor deposition or other coating processes. It should be understood that other types of reflective coatings may alternatively be used. The materials described above permit reflectors 156, 158 to be very inexpensive, to be used without having a high degree of manufacturing precision and assembly alignment, and provide a high percentage of reflectance.

Interference filter 160 is configured to filter out ambient light and other unwanted wavelengths (i.e., wavelengths outside the absorption band of the gas being monitored) from the altered IR energy beam 202. For example, interference filter 160 would be centered at 4.26 micrometers when used to monitor $CO_2$ concentrations. However, interference filter 160 need not be a very precise filter such as a very narrow band-pass filter. As is well-known in the art, other gases comprising the patient's respiratory gases have absorption wavelength bands sufficiently different from $CO_2$ such that interference filter 160 centered at 4.26 micrometers would not significantly pass possible absorption wavelengths corresponding to other gases.

Detector 162 is configured to sense a filtered beam, outputted from interference filter 160, impinging thereon and to convert the impinging filtered beam to an electrical signal (i.e., the analog signal) proportional thereto to be sent to gas concentration generation unit 56 for signal processing. Detector 162 can be any one of a variety of IR sensing devices including a lead selenide (PbSe) type detector, a pyroelectric type detector, and a thermopile type detector.

As shown in FIG. 5, mainstream device 150 "snaps" onto airway adapter 100. Connection section 106 of airway adapter 100 contacts first and second reflectors 156, 158 such that an optical path is available from IR source 154, through the patient's respiratory gases, and to detector 162 without diverting the patient's respiratory gases out of patient respiratory circuit 16 nor coming into direct contact (and thereby contaminating or otherwise altering) with the patient's respiratory gases.

IR energy beam 200 outputted from IR source 154 travels upward to impinge on the inwardly facing curved side of first reflector 156. Due to the curvature and reflective nature of first reflector 156, IR energy beam 200 is reflected to travel through the first of windows 110, the patient's respiratory gases, and then the second of windows 110, to exit on the other side of airway adapter 100. While traveling through airway adapter 100, some of the IR energy beam 200 is absorbed by the patient's respiratory gases (including absorption of beam 200 that is around and at 4.26 micrometers wavelength in the case of $CO_2$ monitoring). The remainder of IR energy beam 200 continues through the second of windows 110 (i.e., the altered IR energy beam 202) and is reflected by the second reflector 158 down to interference filter 160 and finally to detector 162.

To keep main stream analyzer system 22 as inexpensive as possible, it preferably does not include reference filters or self-calibration components. Instead, main stream analyzer system 22, preferably the electrical or analog signal outputted from detector 162 (i.e., a main stream signal) and transmitted to unit 56 for signal processing, is calibrated using the electrical or analog signal outputted from analyzer 28 (i.e., a side,stream signal). Processor 42 correlates a plurality of main stream signals with the corresponding plurality of side stream signals to determine a correlation pattern between the two sets of signals. This correlation pattern is used to adjust accordingly subsequent main stream signals until the next calibration occurs. The calibration process can be completed within two breath time of patient 12 (i.e., approximately 20 seconds).

The calibrated main stream signals outputted to operator console 44 will contain all the corrections that side steam devices are valued for, such as correction of gas interference, pressure change, temperature change, manufacturing tolerance, component limitations, and any other sources for errors without system 22 even having to be factory calibrated. Once main stream analyzer system 22 is calibrated, side stream circuit 54 can go into standby mode and thereby reduce disruptions to patient respiratory circuit 16 (i.e., diverting portions of patient's respiratory out of circuit 16).

System 10 is further configured to re-correlate and provide new calibration parameters to maintain accuracy of gas concentrations generated from mainstream device 150. Recalibratiorn can occur periodically automatically, upon user request, when a change, in system 10 or surroundings is sensed (such as pressure or temperature change), when calibrated main stream signals are impossible values (such as a negative gas concentration value), and/or for any other reason.

Thus, by adding a low cost main stream gas analyzer system 22 to a conventional side stream system, the user reaps the advantages of both types of devices with negligible increase in dollar cost. Since main stream gas analyzer system 22 minimizes the use of metal components or a heater, system 22 is allowed to equilibrate with room temperature and only subsequent changes in room temperature would be a reason to recalibrate. Moreover, the materials and dimensions of components comprising system 22 are chosen such that manufacturing tolerances are large and post-assembly alignment is negligible.

While the embodiments and application of the invention illustrated in the figures and described above are presently preferred, it should be understood that these embodiments are offered by way of example only. For example, although shown in a medical application with a patient, it could alternatively be used for analyzing gases in any gas stream. In another example, more than one main stream system may be utilized within system 10, in which each main stream system is configured to analyze a different gas. Accordingly, the present invention is not limited to a particular embodiment, but extends to various modifications that nevertheless fall within the scope of the appended claims.

What is claimed is:

1. A gas analyzer system, comprising:
   an airway adapter including an entering window and an exiting window to permit non-invasive monitoring of a gas stream;
   a first gas analyzer including a curved component for directing an analyzing beam successively through the entering window, the gas stream, and the exiting window, wherein the curved component of the first gas analyzer couples to the airway adapter and wherein the first gas analyzer measures a first parameter;
   a second gas analyzer, wherein the second gas analyzer measures a second parameter; and a processor, wherein the processor determines a correlation pattern between the measurements of the first gas analyzer and the second gas analyzer using the measurements of the first gas analyzer and the second gas analyzer, and wherein the correlation pattern is used to adjust subsequent measurements of the first gas analyzer.

2. The system of claim 1, wherein the first gas analyzer includes an another curved component, the another curved component configured to direct the analyzing beam exiting the exiting window to a detector.

3. The system of claim 2, wherein the first gas analyzer includes an infrared source positioned proximate to the curved component and configured to generate the analyzing beam.

4. The system of claim 2, wherein the first gas analyzer includes the detector positioned proximate to the another curved component and configured to receive the analyzing beam exiting the exiting window and to output an electrical signal proportional thereto.

5. The system of claim 4, wherein the analyzing beam exiting the exiting window is filtered by an interference filter included in the first gas analyzer before impinging on the detector.

6. The system of claim 5, wherein the interference filter is centered at around 4.26 micrometers.

7. The system of claim 2, wherein the another curved component is similar to the curved component in at least one of shape, material, and beam directing quality.

8. The system of claim 1, wherein the first gas analyzer does not include a heater.

9. The system of claim 1, wherein the entering and exiting windows have transmittance characteristics around 4.26 micrometers wavelength.

10. A system for analyzing a gas stream of interest, comprising:
a side stream system coupled to the gas stream of interest; and
a main stream system coupled to the gas stream of interest and configured to selectively place the side stream system on standby mode, wherein the side stream system is configured to go into active mode as needed to divert a portion of the gas stream of interest to perform calibration of the main stream system by determining a correlation pattern between data values measured by the main stream system and data values measured by the side stream system by using the data values measured by the main stream system and the data values measured by the side stream system.

11. The system of claim 10, wherein the main stream system includes an airway adapter coupled to a main stream device.

12. The system of claim 11, wherein the airway adapter includes an entering window and an exiting window to permit non-invasive monitoring of the gas stream of interest, and the main stream device includes a first and a second curved component, wherein the first and second curved components are configured to couple with the entering window and the exiting window, respectively.

13. The system of claim 12, wherein the main stream device includes a source, a filter, and a detector, an optical path subscribed in successive order by the source, the first curved component, the entering window, the gas stream of interest, the exiting window, the second curved component, the filter, and then the detector to output the sensed signal.

14. The system of claim 13, wherein the entering and exiting windows have transmittance characteristics around 4.26 micrometers wavelength.

15. The system of claim 13, wherein the filter is centered at around 4.26 micrometers.

16. The system of claim 10, further comprising an another main stream system coupled to the gas stream of interest and configured to monitor concentration of a gas component included in the gas stream of interest, wherein the gas component is a different gas component than is monitored by the main stream system.

17. The system of claim 10, wherein the sensed signal is used to generate a calibrated sensed signal including corrections for any one of gas interference, pressure change, temperature change, manufacturing tolerance, and component flaws.

18. A gas analyzer system, comprising:
an airway tube;
a main stream gas analyzer having an airway adapter coupled to the airway tube, the airway adapter including an entering plastic window and an exiting plastic window to permit non-invasive monitoring of a gas stream, and a reflector, wherein the reflector comprises a plastic component with a reflective coating, wherein the main stream gas analyzer measures the concentration of a first component of the gas stream;
a side stream gas analyzer coupled to the airway tube, wherein the side stream gas analyzer measures the concentration of a second component of the gas stream; and
a processor, wherein the processor determines a correlation pattern between the measurements of the main stream gas analyzer and the side stream gas analyzer by using the measurements of the main stream gas analyzer and the side stream gas analyzer, wherein the correlation pattern is used to adjust subsequent measurements of the main stream gas analyzer.

19. A patient respiratory monitoring system, comprising:
a patient respiratory circuit including an airway tube and a respirator;
a main stream gas analyzer having an airway adapter coupled to the airway tube, the airway adapter including an entering plastic window made of a polycarbonate plastic film and an exiting plastic window made of a polycarbonate plastic film to permit non-invasive monitoring of a gas stream, and first and second parabolic reflectors, wherein the reflectors each comprise a plastic component with a reflective coating, wherein the main stream gas analyzer measures a carbon dioxide concentration of the gas stream;
a side stream gas analyzer coupled to the airway tube, wherein the side stream gas analyzer measures the concentration of a component of the gas stream; and
a gas concentration generation unit that receives input signals from the main stream gas analyzer and the side stream gas analyzer, wherein the gas concentration generation unit determines a correlation pattern between the measurements of the main stream gas analyzer and the side stream gas analyzer by using the measurements of the main stream gas analyzer and the side stream gas analyzer, wherein the correlation pattern is used to adjust subsequent measurements of the main stream gas analyzer.

* * * * *